(12) United States Patent
Ferguson

(10) Patent No.: US 10,708,990 B1
(45) Date of Patent: Jul. 7, 2020

(54) COLOR TUNABLE MEDICAL HEADLAMP BEZEL

(71) Applicant: RIVERPOINT MEDICAL, LLC, Portland, OR (US)

(72) Inventor: John Thomas Ferguson, Portland, OR (US)

(73) Assignee: RIVERPOINT MEDICAL, LLC, Portland, OR (US)

( * ) Notice: Subject to any disclaimer, the term of this patent is extended or adjusted under 35 U.S.C. 154(b) by 169 days.

(21) Appl. No.: 15/892,768

(22) Filed: Feb. 9, 2018

(51) Int. Cl.
| | |
|---|---|
| *H05B 45/20* | (2020.01) |
| *F21L 4/02* | (2006.01) |
| *F21V 29/15* | (2015.01) |
| *A61B 90/35* | (2016.01) |
| *A61B 90/50* | (2016.01) |
| *F21Y 115/10* | (2016.01) |
| *F21W 131/20* | (2006.01) |
| *F21Y 113/17* | (2016.01) |

(52) U.S. Cl.
CPC ............. *H05B 45/20* (2020.01); *A61B 90/35* (2016.02); *F21L 4/02* (2013.01); *F21V 29/15* (2015.01); *A61B 2090/502* (2016.02); *F21W 2131/20* (2013.01); *F21Y 2113/17* (2016.08); *F21Y 2115/10* (2016.08)

(58) Field of Classification Search
CPC ............. F21V 21/084; A61B 2090/502; A61B 1/0692; A61B 5/6814; F21L 15/14; A42B 3/044; A42B 3/0446; A61N 2005/0647
See application file for complete search history.

(56) References Cited

U.S. PATENT DOCUMENTS

| | | | |
|---|---|---|---|
| 7,192,151 B2 | 3/2007 | Clupper et al. | |
| 7,450,028 B2 | 11/2008 | DeGodzinsky | |
| 9,500,340 B2 | 11/2016 | Stone et al. | |
| RE46,325 E | 2/2017 | Swayne et al. | |
| 2010/0071904 A1* | 3/2010 | Burns | C10G 21/22 166/302 |
| 2012/0032588 A1* | 2/2012 | Lin | F21V 29/673 315/32 |
| 2012/0320568 A1 | 12/2012 | Chang | |
| 2013/0039048 A1* | 2/2013 | Lo | F21V 29/004 362/184 |

(Continued)

OTHER PUBLICATIONS

Colblindor, Deuteranopia—Red-Green Color Blindness, http://www.colorblindness.com, Mar. 5, 2014.

*Primary Examiner* — Anh T Mai
*Assistant Examiner* — Zachary J Snyder
(74) *Attorney, Agent, or Firm* — Timothy E. Siegel Patent Law, PLLC; Timothy E. Siegel

(57) ABSTRACT

A color-adjustable medical headlamp assembly, including a headband assembly and a bezel, which can be worn around a user's head. The bezel contains a light source assembly that is capable of generating light with different colors and intensities, and an optical train that focuses the light generated by the light source assembly. A user input assembly is included to allow for the selection and adjustment of both the color and brightness of the light from the bezel. Also, the rear surface of the bezel has a higher coefficient of thermal conductance compared to the movable portion of the bezel and is an avenue for heat dissipation. Finally, a heat shield is attached to the bezel to cover its rear surface, which can pose a burn hazard after prolonged usage.

14 Claims, 4 Drawing Sheets

(56) References Cited

U.S. PATENT DOCUMENTS

2014/0334159 A1* 11/2014 Ferguson ............... A61B 90/35
362/311.02
2015/0073227 A1* 3/2015 Teder ....................... A61B 1/06
600/249

* cited by examiner

COLOR TUNABLE MEDICAL HEADLAMP BEZEL

BACKGROUND

Medical lighting of different colors can provide various benefits. Distinguishing various tissue types, assisting a color-blind surgeon or simple personal preference may cause a color blend that is optimal for a first surgeon, in a first situation, is not optimal for a second surgeon in a second situation.

Another problem in the design of medical headlamp assemblies is that of exhausting heat from the bezel (also referred to as "headlamp"). A typical bezel is only about the size of an acorn, with limited surface to radiate heat. If the surface area becomes too hot, it creates a burn hazard. While LEDs do not heat up as much as other conventional light sources, the use of an LED assembly would still cause the temperature of surrounding areas within the bezel to increase, especially during medical operations that span hours.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In a first aspect, the present invention relates to a medical headlamp assembly, comprising a headband assembly adapted to fit around a user's head, and a bezel that is connected to and supported by a linkage to the headband assembly. The bezel includes a light source assembly that is capable of producing light of differing colors and intensities, and an optical train that focuses the light generated by the light source assembly. A user input assembly is also included to permit user control over the color and intensity from the bezel.

In a second aspect, the present invention relates to a medical headlamp assembly, comprising a headband assembly adapted to fit around a user's head, and a bezel connected to and supported by a linkage to the headband assembly. The bezel includes a housing that comprises a stationary portion and a moveable portion, where the moveable portion acts to adjust some element of the bezel and has an exterior surface. The bezel further includes a light source assembly to generate a light beam, and an optical train for focusing the light beam from the bezel, both of which are held within the housing. The rear surface of the bezel, which is part of the stationary portion, has a higher coefficient of thermal conductance than the exterior surface of the moveable portion; the rear surface of the bezel heats up more readily compared to the exterior surface of the moveable portion and provides an avenue for heat dissipation. Lastly, a heat shield is attached to the bezel and covers the rear surface of the bezel to protect a user from possible burns.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced drawings. It is intended that the embodiments and figures disclosed herein are to be considered illustrative rather than restrictive.

DETAILED DESCRIPTION OF THE PREFERRED EMBODIMENTS

Figure 1:
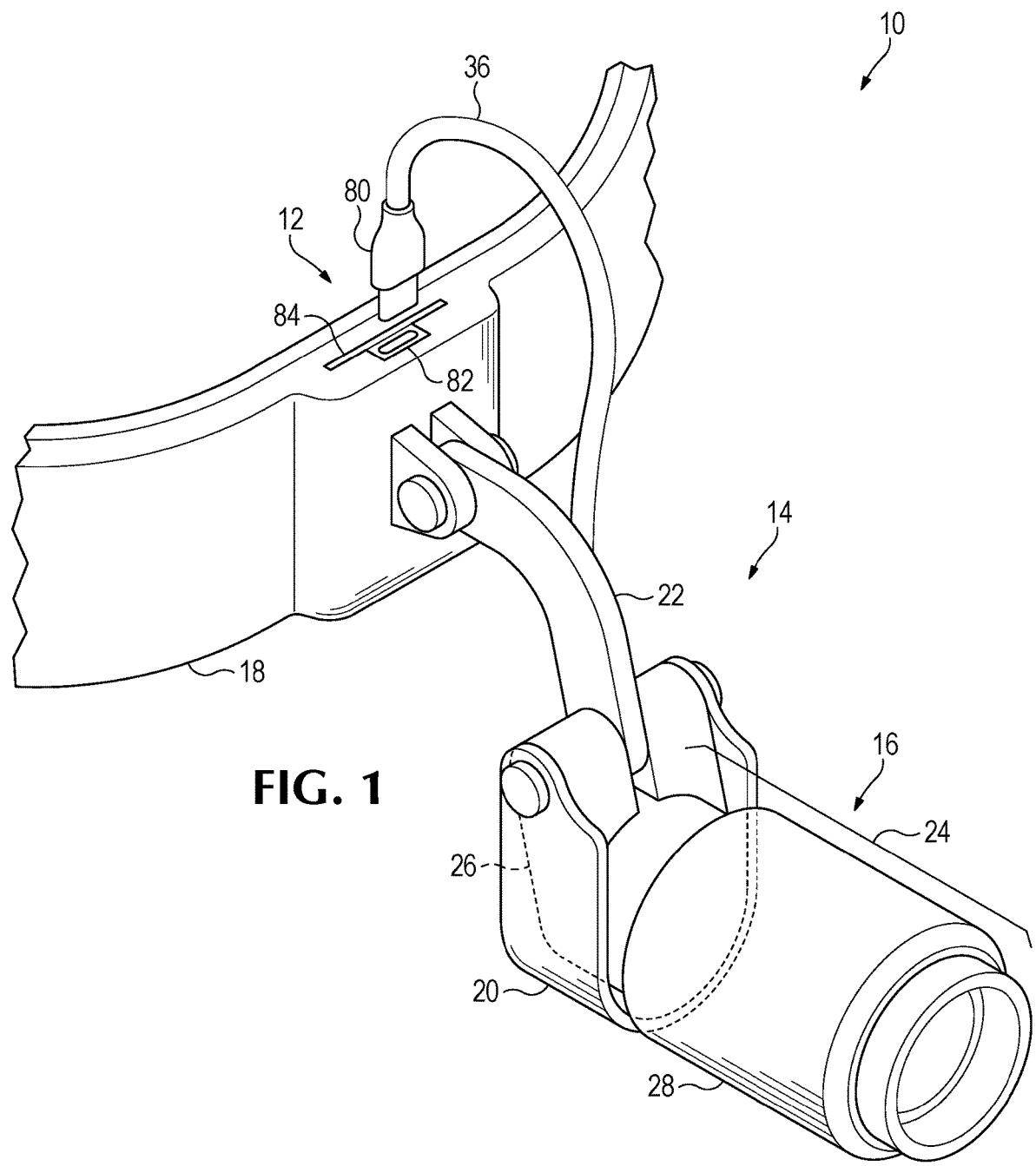
FIG. 1 is an isometric detail view of the bezel and headband connection area, of the headlamp assembly of FIG. 1.

In a preferred embodiment of a medical headlamp assembly 10, according to the present invention, a headband assembly 12 supports bezel 16 (FIG. 1). The medical headlamp assembly 10 includes a headband 18, a bezel 16, and a heat shield 20 positioned at the back of, and attached to, the bezel 16, as is described further below, in reference to FIG. 4. Bezel 16 is attached to headband 18 via linkage 22.

Figure 2:
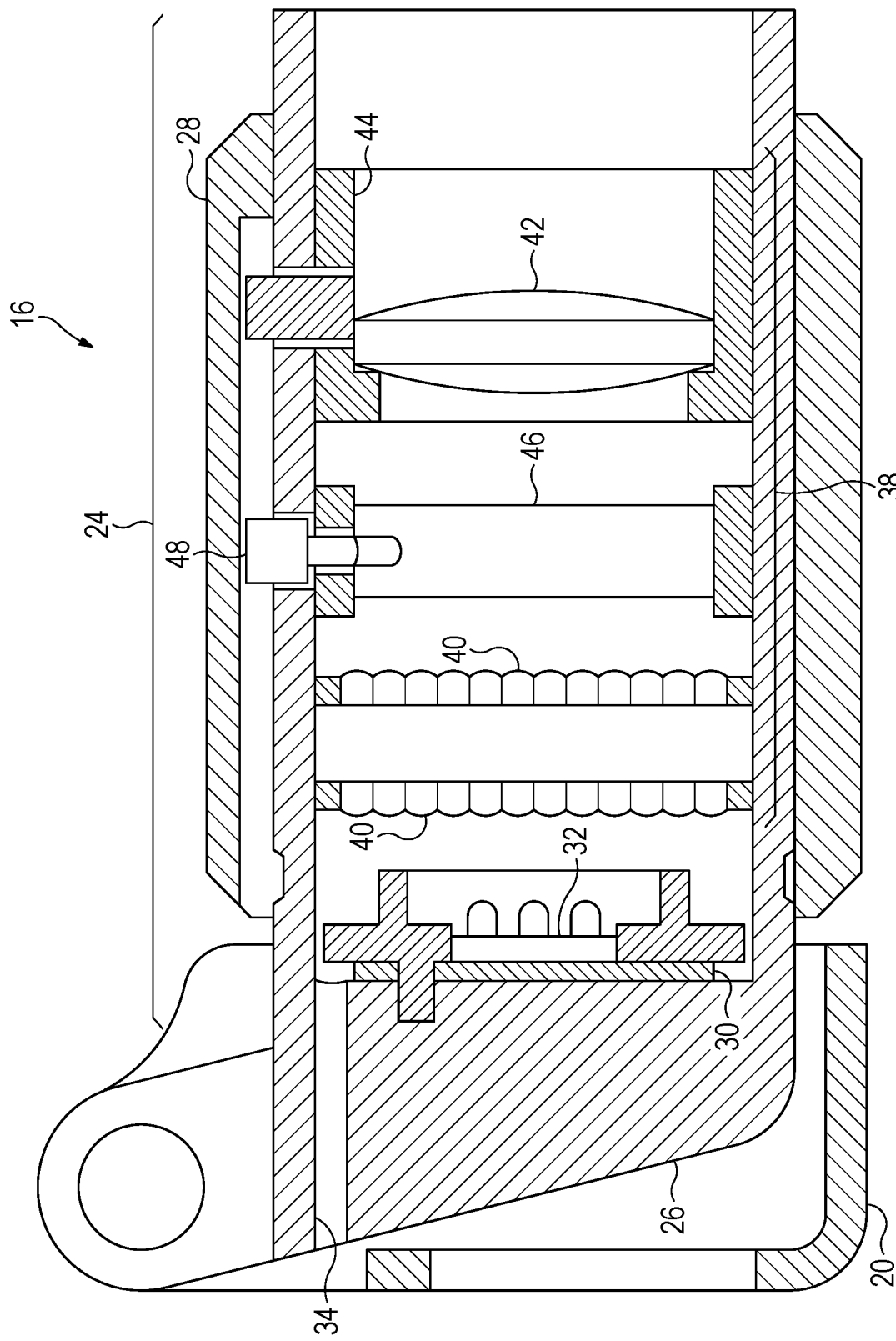
FIG. 2 shows a sectional view of the bezel of FIG. 1.

Referring to FIGS. 1 and 2, a bezel 16 is connected to the headband assembly 18 through linkage 22. The bezel 16 includes a housing 24, which comprises a stationary portion 26, and a moveable portion in the form of an outer ring 28. The stationary portion 26 houses a piece of circuit 30 with conductive traces (not shown) that are adapted to power a light source assembly 32, which is described below. The stationary portion 26 defines a channel 34, which allows for the insertion of a first end of cable 36 to supply electricity to the conductive traces. In a preferred embodiment, the second end of cable 36 is a USB connector 80, which can be inserted into USP port 82 and establish electrical connection between light source assembly 32 and circuit board 84. Circuit board 84 is included to permit color and intensity control over light source assembly 32, which will be described in greater detail below.

Again, referring to FIG. 2, light source assembly 32 is positioned at the back of and extends into the interior cavity of stationary portion 26. An optical train 38 is positioned in front of light source assembly 32. The optical train 38 includes a series of fly-eye lens arrays 40, and an exit lens 42 that is held by an exit lens holder 44, which in turn is surrounded and held by outer ring 28. During operation, the light generated by light source assembly 32 passes through optical train 38 to produce a light beam with a substantially homogenous intensity.

In preferred embodiments, the size of the light beam is adjustable as required for various applications. As illustrated in FIG. 2, the optical train 38 can further include an iris 46 adjustable by actuator 48, positioned between the fly-eye lens arrays 40 and the exit lens 42, which focuses the light beam generated by light source assembly 32. The beam radius can be further tuned by changing the position of the exit lens 42 within housing 24. In preferred embodiments, adjustment of the iris 46 by actuator 48 and the positioning of exit lens 42 within housing 24 are both coupled to the rotational motion of outer ring 28, such that the beam size is adjusted when the user rotates outer ring 28. In an alternative preferred embodiment, iris 46 is not present, and the beamwidth is adjusted solely by focusing (moving) the exit lens 42.

Figure 5:
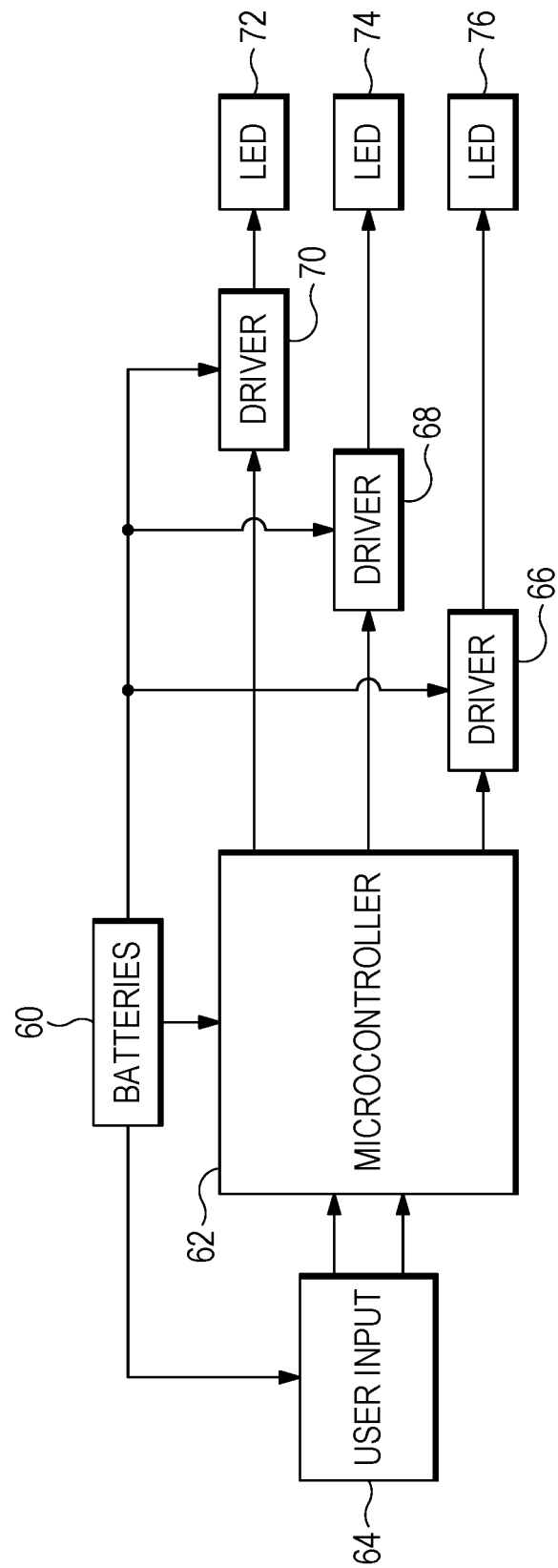
FIG. 5 is a block diagram of the electronics of the medical headlamp assembly of FIG. 1.

Referring to FIG. 5, batteries 60 (typically attached to headband assembly 12) power a microcontroller 62 (located on circuit board 84 (shown in FIG. 1)), which receives input from a user input device 64, commanding color and brightness. In response microcontroller 62 controls LED drivers 66, 68 and 70 (also located on circuit board 84), which power LEDs 72, 74 and 76, respectively, in light source assembly 32 (FIG. 2). LED drivers 66, 68 and 70 are, in one embodiment, DC-to-DC converters, but could also be pulse width modulated drivers or some other type of device that has a controllable, variable power output. In other embodiments, a fourth LED is added, producing amber, or white, light.

The three LEDs, 72, 74 and 76, chosen so that varying the light output of the LEDs 72, 74 and 76, can produce any color of visible light. Also, a broad range of spectra may be produced, by varying the power to the three LEDS 72, 74, and 76. In one embodiment, the three LED's colors are red, green and blue, but in another preferred embodiment, the three LED colors are cyan, purple and yellow. In another embodiment, two LEDs are chosen to be at the extremes of the visible light spectrum, red and violet, with the third in the middle (green or cyan). The LEDs are controlled to produce a broad choice of beam spectra, to achieve not only a certain beam color, but also different reflective characteristics. Although two beams may appear to be exactly the same to a human observer, because each one stimulates the retinal cones equally, the reflections from tissue of the two beams may be different, if a spectrum has less light of a frequency that reflects from a particular type of tissue. By careful selection of a spectrum, it is possible to provide a greater degree of color contrast between different types of tissue.

For example, the beam spectrum can be selected such that when used to illuminate a biological structure, the light beam causes one tissue type to contrast with a second tissue type (i.e. enhancing the color difference between healthy tissue and focal tissues upon illumination, optimally illuminating various tissue types such as skin, muscle, fat, blood vessels, and organs). In the case in which the LED assembly comprises a red LED, a green LED, and a violet LED, the red and the violet LEDS may be illuminated at maximum power, and the green LED not used, to accentuate color contrast between different types of tissue, having different reflective characteristics, with one tissue type being more reflective of low frequency light (red tissue) and other tissue being more reflective of high frequency light (bone, which appears to have more reflectance across the spectrum). As another example, the colors of the LEDs can be selected such that light source assembly 32 emits light with a lower intensity within the range of 500 nm-590 nm, as opposed to light within the range of 420 nm-470 nm or in the range 590-700 nm; a beam having this spectral profile would be suitable for users with deuteranopia (red-green color blindness), as they have a reduced ability to see light in the 470 to 590 nm range. In one embodiment a spectrum is chosen to highlight a dye injected to show a particular feature or diseased portion of an organ. In embodiments, an ultraviolet or infrared LED is included in assembly 32, to cause fluorescence of a dye, or some other effect. The use of agents can be used to identify diseased tissue and may also be used to identify locations of hemorrhage during surgery. In embodiments, different spectra are interleaved over time, so that a surgeon can periodically obtain a view highlighting a dye or other sort of agent, and then resume a view illuminated, for example, by white light. In one embodiment, white light illumination is interrupted every minute, for five seconds, by a beam spectrum designed to highlight a particular type of tissue or particular dye that has been previously injected. In another embodiment, white light illumination is interrupted every three minutes, for five seconds with special-purpose spectrum.

In preferred embodiments of the present invention, both the color and the brightness of the light beam are adjustable through a user input assembly 64. In some embodiments, the user input assembly 64 forms part of headband 18 and is electrically coupled to the microcontroller 62, which is physically located on circuit board 84. In one such embodiment, the user input assembly 64 includes control knobs (not shown) that are coupled to the microcontroller 62. For instance, a brightness control knob can be used to simultaneously adjust the brightness of the LEDs 72, 74 and 76, thereby controlling the overall intensity of the light beam from the bezel 16, while a color control knob is used to vary the color of the light beam, by changing the proportion of light produced by each LED 72, 74 and 76. In an alternative embodiment, a separate power control knob is provided for each LED 72, 74 and 76.

In one embodiment, the user input assembly 64 additionally includes user-pre-set color spectra, that are configured to provide contrast between certain tissue types, or to highlight a particular tissue type, such as bone. In embodiments, a set of buttons (not shown) are provided on the head strap, each one activating a different preset color spectrum. In certain embodiments, the preset color spectra can be customized. For example, each preset spectrum button can be configured so that if it is held down for an extended period (for example, 2 seconds), the preset spectra that is selected by that button can then be set by whatever system is made available for adjusting the light beam spectrum, for example a set of knobs. After adjusting the knob(s) until a desired spectrum is achieved, another extended-period press of that button would enter that spectrum into memory (of microcontroller 62), so that it can be reselected at the push of that button. In one embodiment, some buttons are provided that are not pre-loaded with a preset spectrum, to permit the user to add preset spectra of his choosing, without erasing a factory-set spectrum.

In alternative embodiments, the user input assembly 64 is installed onto an electronic platform, such as a computer (tablet, laptop or desktop) or a smartphone, and is in wireless communication with the microcontroller 62 on circuit board 84, using a wireless protocol such as Wi-Fi or Bluetooth. A graphical user interface (not shown) permits adjustment of color and brightness of the light beam. This interface can, for example, display a color triangle containing all possible beam colors as determined by the power delivered to each LED 72, 74 and 76 wherein the beam color is selected by the user simply by clicking on, or in the case of a touch-screen, touching, the desired option shown within the color triangle. Alternatively (or concurrently), the graphical user interface can offer the option of manually inserting intensity values (ranging from 0-100%, for example) for the individual LEDs, which can allow for fine control over the resulting color of the light beam. The brightness is adjusted by using a brightness slider, which simultaneously increases or decreases the intensities of all LEDs. The graphical user interface can additionally include the option to select and save user-customizable, preset color spectra as described earlier. To anticipate the situation involving multiple users, the preset color spectra is configured to correspond to individual bezels, and/or to specific LED color combinations, which would change the beam color options. In additional embodiments, the user input assembly 64 includes a voice command device, which permits voice control over the light source assembly 32 through the electronic platform.

While an LED assembly offers flexibility in beam color selection, it may be necessary to swap out the bezel 16 should the medical headband assembly of the present invention be used by multiple users, who may require different beam colors and preset color spectra as dictated by specific tasks, the users' preferences, or their needs. A change in bezel 16 would also be needed if it is damaged, especially during a medical operation. Referring back to FIG. 1, bezel 16 is attached to headband 18 through linkage 22. In preferred embodiments, bezel 16 and linkage 22 can be detached from headband 18 and thereby forming a removable sub-assembly 14 of medical headlamp assembly 10, providing the ease of bezel 16 replacement.

In preferred embodiments, the stationary portion 26 of the housing is constructed from a light-weight metal. Examples of suitable light-weight metals include aluminum, and alloys of aluminum. During operation of medical headlamp assembly 10, heat is generated by light source assembly 32, which is conducted throughout the body and external surface of the bezel 16. As a result, the metallic portions of the bezel 16 pose a burn hazard, especially during extended periods of usage. In order to reduce the risk of burns from touching the surface of the bezel 16 during operation, portions of the bezel 16 can be coated with a material that has a lower coefficient of thermal conduction than the surface of the bezel 16. In a preferred embodiment, a coating is applied to outer ring 28. The coating material is selected from a number of heat-insulating materials, such as, but not limited to, ceramics, polymers, silicones, and mixtures thereof. In preferred embodiments, the coating is a ceramic. In certain embodiments, the ceramic coating is a coating constructed of aluminum oxide, zirconium oxide, or mullite. In other embodiments, the coating is a ceramic coating available from Cerakote®. It is to be appreciated that the coating can be applied to additional areas that will be touched by the user, and thus can be applied to any portion of the exterior surface of the bezel 16 as deemed necessary. In preferred embodiments, the thickness of the coating is less than 0.1 mm. In an alternate embodiment, the outer ring 28 is constructed of a material having a lower coefficient of thermal conductance than the material used to construct stationary portion 26.

As overheating of the interior of bezel 16 and light source assembly 32 is undesirable due to negative effects on device performance and lifetime (i.e. reduction in light output, loss in efficiency, degradation of the LED junction element), effective heat dissipation is necessary. In preferred embodiments of the present invention, the light source assembly 32 is situated against the rear of the interior of stationary portion 26. Due to the proximity to the light source assembly 32, which generates heat during operation of the device, the rear end of bezel 16 would necessarily heat up at a higher rate compared to portions of bezel 16 that are further removed from light source assembly 32. Hence, the surface of this rear end presents an avenue for heat dissipation, especially in embodiments where portions of the external surface of bezel 16 is coated with a heat-insulating material, as described above, which hinders heat dissipation through these portions. In order to simultaneously allow for heat dissipation through the rear surface of bezel 16 and also protect the user from possible burns from touching said surface, a heat shield 20 is attached to bezel 16, as illustrated in FIGS. 1, 2, and 4.

Figure 3:
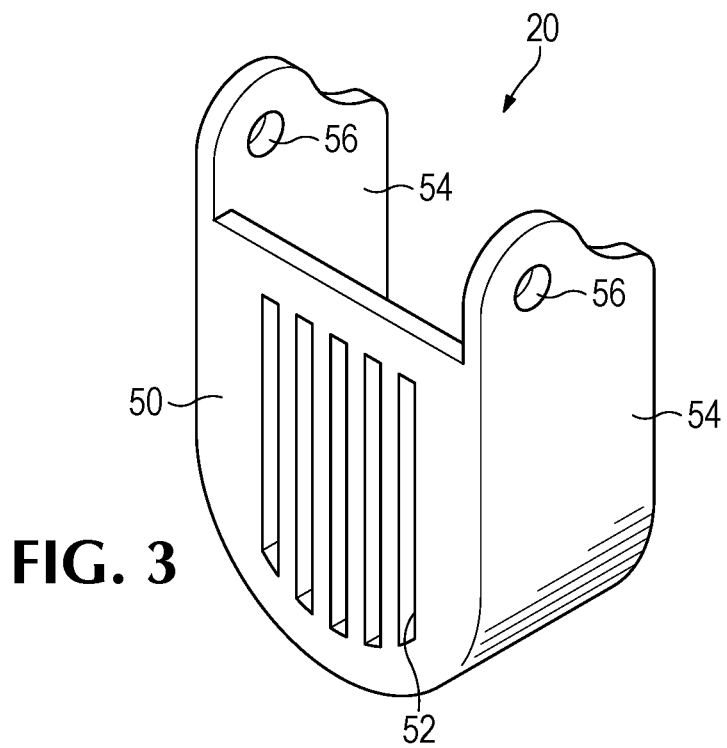
FIG. 3 is an isometric view of the heat shield.
Figure 4:
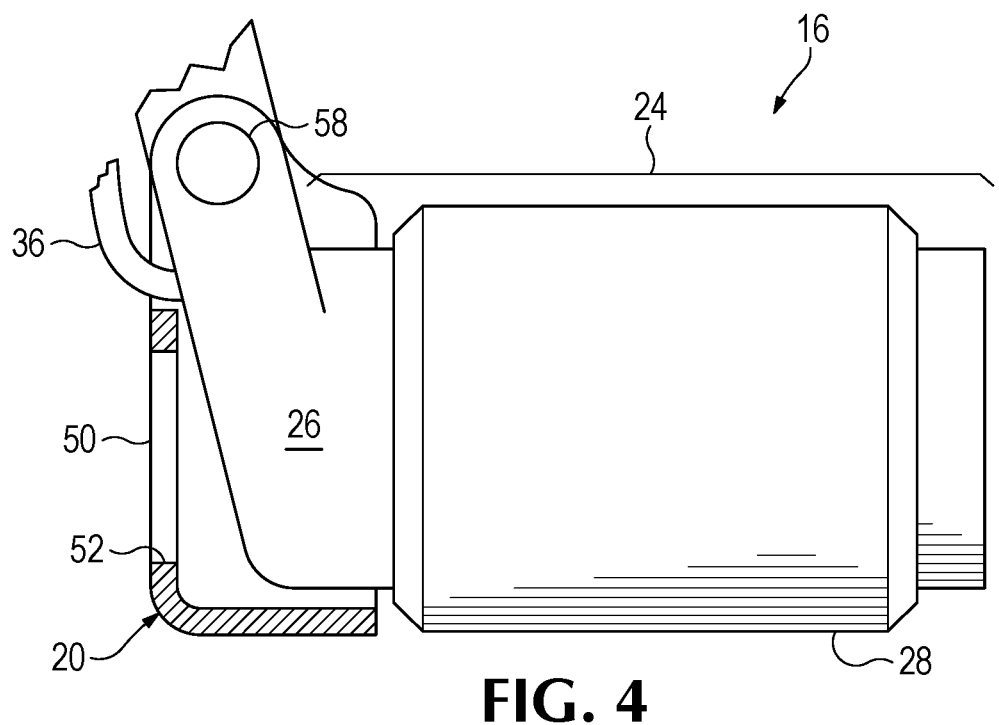
FIG. 4 is a side view of the bezel of FIG. 1, with the heat shield attached, and shown in a sectional view

Referring to FIGS. 3 and 4, heat shield 20 comprises a panel 50 that defines apertures 52 to allow heat to flow from the rear surface of bezel 16 through heat shield 20. Heat shield 20 further comprises a side portion 54, which extends from the outer edge of panel 50 in the direction substantially perpendicular to the plane defined by panel 50 towards bezel 16 and covers the rear portion of bezel 16. In preferred embodiments, side portion 54 extends upward beyond panel 50 and define holes 56, with which heat shield 20 is attached to bezel 16 by coupling to protrusions 58 on bezel 16, having shapes that are complimentary to holes 56. In preferred embodiments, heat shield 20 can be detached from bezel 16 by disengaging holes 56 from protrusions 58. In a preferred embodiment, holes 56 and protrusions 58 are circular in shape, such that heat shield 20, when attached to bezel 16, is moveable and can be repositioned to expose the rear surface of bezel 16.

As heat radiates from the rear surface of bezel 16 and passes through apertures 52, heat shield 20 can also heat up and present a burn hazard, depending on the material used for its construction. Therefore, the heat shield is ideally constructed of a material that is a thermal insulator, such as plastic. Alternatively, the surface of the heat shield 20 is coated with a material having a lower coefficient of thermal conductance than the material used to construct heat shield 20. Non-limiting examples of suitable coating materials include ceramics, polymers, silicones, and mixtures thereof. The coating material is selected from a number of heat-insulating materials, such as, but not limited to ceramics, polymers, silicones, and mixtures thereof. In preferred embodiments, the coating is a ceramic. In certain embodiments, the ceramic coating is a coating constructed of aluminum oxide, zirconium oxide, or mullite. In other embodiments, the coating is a ceramic coating available from Cerakote®. In a preferred embodiment, the thickness of the coating is less than 0.1 mm. As will be appreciated by a person skilled in the art, the appropriate thickness of the coating will depend on the properties of the coating material.

While a number of exemplary aspects and embodiments have been discussed above, those possessed of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

The invention claimed is:

1. A medical headlamp assembly, comprising:
   (a) a headband assembly;
   (b) a bezel connected to and supported by a linkage to said headband assembly, said bezel having a rear surface, and including:
      (i) a housing having a stationary portion and a moveable portion, and wherein said moveable portion acts to adjust some element of said bezel and has an exterior surface and wherein said rear surface of said bezel is part of said stationary portion;
      (ii) a light source assembly and an optical train for focusing said light from said light source assembly, held in said housing; and
   (c) wherein said rear surface of said bezel has a higher coefficient of thermal conductivity than said exterior surface of said moveable portion;
   (d) a heat shield, covering said rear surface of said bezel to protect a wearer from possible burns, and being separate from said moveable portion of said housing, and being made of a material that is a thermal insulator.

2. The medical headlamp assembly of claim 1, wherein said heat shield is moveable, between a first position in which said rear surface is covered and a second position in which said rear surface is exposed.

3. The medical headlamp assembly of claim 1, wherein said heat shield is removable.

4. The medical headlamp assembly of claim 1, wherein said moveable portion includes a first material, and a surface coating that forms said exterior surface and has a lower coefficient of thermal conductance than said first material.

5. The medical headlamp assembly of claim 4, wherein said surface coating is less than 0.1 mm thick.

6. The medical headlamp assembly of claim 4, wherein said coating is ceramic.

7. The medical headlamp assembly of claim 4, wherein the ceramic is aluminum oxide, zirconium oxide, or mullite.

8. The medical headlamp assembly of claim 1, wherein said moveable portion is constructed of a first material, said material having a lower coefficient of thermal conductance than said rear surface of said bezel.

9. The medical headlamp assembly of claim 1, wherein said heat shield defines apertures, to permit a greater flow of heat through said heat shield.

10. The medical headlamp assembly of claim 1, wherein said heat shield is constructed of plastic.

11. The medical headlamp assembly of claim 1, wherein said heat shield includes a first material, and a surface coating applied atop said first material, wherein said coating has a lower coefficient of thermal conductance than said first material.

12. The medical headlamp assembly of claim 11, wherein said surface coating is less than 0.1 mm thick.

13. The medical headlamp assembly of claim 11, wherein said coating is ceramic.

14. The medical headlamp assembly of claim 13, wherein the ceramic is aluminum oxide, zirconium oxide, or mullite.

* * * * *